Figure 1:
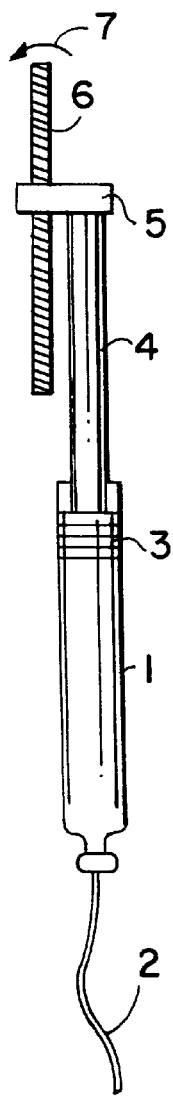

United States Patent [19]

Poulsen et al.

[11] Patent Number: 5,957,889
[45] Date of Patent: Sep. 28, 1999

[54] DISPLACEMENT SYSTEM FOR CONTROLLED INFUSION OF A LIQUID

[75] Inventors: Jens Ulrik Poulsen, Gentofte; Henrik Ljunggreen, Valby; Henning Munk Ejlersen, Vedbaek; Jens Munk, Stenloese; Lars Peter Klitmose, Gentofte; Preben Broskov Nielsen, Copenhagen; Søren Mikkelsen, Ballerup; Jens Møller-Jensen; Anders Heger, both of Copenhagen, all of Denmark

[73] Assignee: Novo Nordisk A/S, Bagsvaerd, Denmark

[21] Appl. No.: 08/615,298

[22] PCT Filed: Sep. 27, 1994

[86] PCT No.: PCT/DK94/00361

§ 371 Date: Aug. 29, 1996

§ 102(e) Date: Aug. 29, 1996

[87] PCT Pub. No.: WO95/09021

PCT Pub. Date: Apr. 6, 1995

Related U.S. Application Data

[63] Continuation of application No. PCT/DK94/00361, Sep. 27, 1994.

[30] Foreign Application Priority Data

Sep. 27, 1993 [DK] Denmark .................................. 1092/93

[51] Int. Cl.⁶ .................... A61M 37/00; A61M 5/315; A61M 5/145
[52] U.S. Cl. ................ 604/131; 604/218; 604/211
[58] Field of Search ......................... 604/131, 151, 604/152, 181, 218, 208–11, 154, 155, 224; 128/DIG. 1

[56] References Cited

U.S. PATENT DOCUMENTS 4,276,878  7/1981  Stroz ...................... 128/218
4,298,000  11/1981 Thill et al. ................ 604/135
4,313,439  2/1982  Babb et al. .............. 604/135 X
4,381,006  4/1983  Genese ..................... 604/135
4,493,704  1/1985  Beard et al. .............. 604/154
4,676,122  6/1987  Szabo et al. ............ 604/135 X
5,044,222  9/1991  Tanaka et al. .
5,064,098  11/1991 Hutter, III et al. ............. 222/137
5,637,095  6/1997  Nason et al. ............... 604/135

FOREIGN PATENT DOCUMENTS 0 110 687  6/1984   European Pat. Off. .
   893471  7/1944   France .
  1124613  10/1956  France .
  1200405  12/1959  France .
   212625  12/1960  Germany .
33 31 424  3/1984   Germany .

*Primary Examiner*—Danton D. DeMille
*Attorney, Agent, or Firm*—Steve T. Zelson, Esq.

[57] ABSTRACT

In a displacement system for controlled infusion of a liquid from a cartridge comprising a tubular vessel (1), which is at a rear end closed by a piston (3) which may be forced by a piston rod (8) moving into the vessel (1) in the axial direction thereof to press out the liquid through an outlet (2) arranged at a front end of the vessel (1), the piston rod (8) is provided as a flexible incompressible construction which is by a piston rod guide (9) behind the rear end of the cartridge deflected away from the axis of this cartridge, preferably 180°. The piston rod guide (9) has a guiding track comprising a curved part and linear parts at each end of the curved part ensuring that the piston rod is guided along a length (a) in the direction of the axis of the cartridge which length (a) is longer than the distance (b) between the two axes of the piston rod parts projecting from the piston rod guide. The guiding track is further elaborated to the very shape which the curved part of the piston rod will spontaneously adopt when its end portions are kept parallel.

11 Claims, 1 Drawing Sheet

DISPLACEMENT SYSTEM FOR CONTROLLED INFUSION OF A LIQUID

CROSS-REFERENCE TO RELATED APPLICATIONS

This application is a continuation of PCT/DK94/00361 filed Sep. 27, 1994, which is incorporated herein by reference.

The invention relates to displacement systems for controlled infusion of a liquid from a cartridge of the kind comprising a tubular vessel, which is at a rear end closed by a piston which may be forced by a piston rod into the tube to press out the liquid through an outlet arranged at a front end of the tube.

Designated as pumps such displacement systems are used for therapeutic infusion of medicine, e.g insulin for diabetics to whom the natural production of insulin is simulated in this way.

A commonly used pump structure comprises a housing with a cavity accommodating an infusion syringe cartridge having a piston and a piston rod by which the piston may be forced into the cartridge to press out the medicament in the cartridge through an outlet at the end of the cartridge opposite the piston. Such infusion pumps, which are based on the technique known from syringes by which the dosage can be adjusted with very close accuracy, has many advantages. They are simple in their construction and a precise indication of the medicine left in the cartridge may currently be obtained by monitoring the position of the piston in the cartridge, and in the same way the amount infused can be very precise controlled by controlling the distance of movement of the piston in the cartridge.

A heavy drawback by the pumps of the cartridge and piston type is the fact that at least one of the dimensions of the pump have to be at least more than two times the overall stroke of the piston in the cartridge as the cartridge has to be at least a little longer than this stroke and as space must be reserved for the piston rod behind the cartridge when the piston in a new cartridge is in its rearmost position. Thereby a limit is set for the extent of the miniaturization which is aimed at to make it as comfortable as possible to carry the pump during the activities of a day.

Consequently it is an object of the invention to provide a displacement system of the cartridge/piston type wherein this drawback is avoided.

This is obtained by a displacement system of the kind mentioned in the ingress of this specification and which system is according to the invention characterized in that the piston rod is provided as a flexible incompressible construction and at a position behind the rear end of the cartridge is deflected away from the axis of the cartridge.

The deflection of the piston rod away from the axis of the cartridge may be obtained by a piston rod guide being provided behind the rear end of the cartridge. The piston rod guide governs the deflection of the piston rod so that this rod will only be deflected in the way determined by the guide.

Preferably the piston rod is deflected 180° so that it forms two parallel straight portions extending from the piston rod guide.

To ensure that the necessary deflecting forces on the piston rod are exerted by the guide alone so that the straight portions projecting from the guide are parallel without any need for deflecting forces on these projecting portion, the piston rod guide has a guide track having an upper curved part and a lover linear part at each end of the curved part and having a length in the direction of the projecting parallel portions, which length taken from the ends of the guide track from which these portions projects to the centre of the piston rod at the top of the curved part is equal to or larger than the distance between the axes of the projecting parallel portions.

It is also important that the piston rod is abutting the curved guiding surface all the way so that the spring effect of the piston rod does not cause any slack in the guiding as such a slack may result in an imprecise dose. This continuous abutment is obtained by elaborating the curved part of the guide in accordance with the shape which the curved part of the piston rod will spontaneously adopt when its end portions are kept parallel.

The piston rod may be made flexible in several ways. By being a flexible band stiffened by having an arcuate cross section the piston rod has one preferred mode of deflection as it will tend to deflect towards the concave side of the arcuate cross section. A special stiff piston rod may be obtained when two of the mentioned bands are combined with their convex sides abutting each other over the distance between the piston and the point of deflexion. When the piston rod is deflected, the two bands are deflected in different directions away from each other as each band is deflected toward the concave side of its cross section. The piston rod guide must be accordingly designed to ensure this splitting of the flexible piston rod.

Alternatively the piston rod may be a flexible helix with narrowly adjacent turns of windings. This piston rod has no preferred mode of deflection and may be guided in any direction by the piston rod guide.

From SE 449 776 is known a device in which a piston is moved by transmitting a pulling or pressing force through a flexible helix. During the working function of the device the provided flexible piston rod is used for exerting a pulling force on a piston to very slowly suck a fluid, preferably air, into a cylinder ampoule to obtain a sample representative of the ambient air over a time. The piston rod may further be used for pressing the sample out of the cylinder ampoule. It is mentioned that the wire used and the helix must be so dimensioned that the straight portion of the piston rod does not bend out when transmitting a pressing force through this portion and so that the windings are not pulled apart to leave lasting deformation of the helix when a pulling force is transmitted.

When the piston rod according to the invention is a flexible helix, care must be taken to ensure that the helix is so dimensioned that it may transmit an axial pressing force without being compressed and without bending out as any bending out means imprecise dosage. This is avoided by keeping the coiling ratio, i.e. the ratio between the outer diameter of the helix minus the diameter of the wire and the diameter of the wire from which the helix is wound, within certain limits.

Also the initial tension, which keeps the windings of the helix abutting each other even when a pulling force is transmitted by the helix, is of importance to the compressibility of the helix. The larger the initial tension the smaller the tendency for one winding to slip on the adjacent winding to start a bending out. Consequently the initial tension should be maximised.

As the pulling of the piston rod only serves the retraction of the piston rod to its initial position when a new cylinder ampoule is inserted, no heavy pulling force is transmitted and the demands to the precise transmission are low, but the transmission of pressing forces have to be very precise and no compression or bending out of the piston rod can be tolerated.

These problems are all overcome by a piston rod wound as a helix with a coiling ratio $$r_{coil} = \frac{d_{helix} - d_{wire}}{d_{wire}} < 5.0$$

where $d_{helix}$ is the outer diameter of the wound helix, and $d_{wire}$ is the diameter of the wire.

Preferably $r_{coil}$ is kept <4.5, more preferably <4.0, and most preferably <3.5.

Further the piston rod may be a series of interconnected chain links. Such a rod may have a preferred mode of deflection or may be freely deflected in any direction, all depending on the construction and the interconnection of the chain links.

When the piston rod is a flexible band this band may be cogged along one or both of its sides to provide a rack which may be engaged by a driving pinion to move the piston rod and consequently the piston into the vessel to press out an amount of the medicine in the cartridge.

When the piston rod is provided as a narrowly wound helix the windings of this helix may present an external thread, which may be engaged by an internally threaded nut element which will drive the piston rod into the cartridge when this nut element is rotated and is not axial displaceable in the housing accommodating the cartridge, the piston rod guide, and a drive mechanism.

A piston rod constructed from interconnected chain links may be driven by either of the mentioned ways as each chain link may be provided by either a part of an external thread or with teeth making it a part of a rack.

The driving force is preferably transmitted to the piston rod at a linear part thereof as the pitch of the rack or the thread are only unambiguously defined at such linear parts.

Preferably the driving force is transmitted to the piston rod immediately behind the cartridge at a position between the cartridge and the piston rod guide. Thereby transmission through the non-linear part of the piston rod is avoided.

Alternatively a driving force may applied by an advancing mechanism at the free end of the piston rod exerting a pressing force in the axial direction of this free end. Thereby inaccuracies caused by possible compressions in the piston rod are eliminated.

Figure 2:
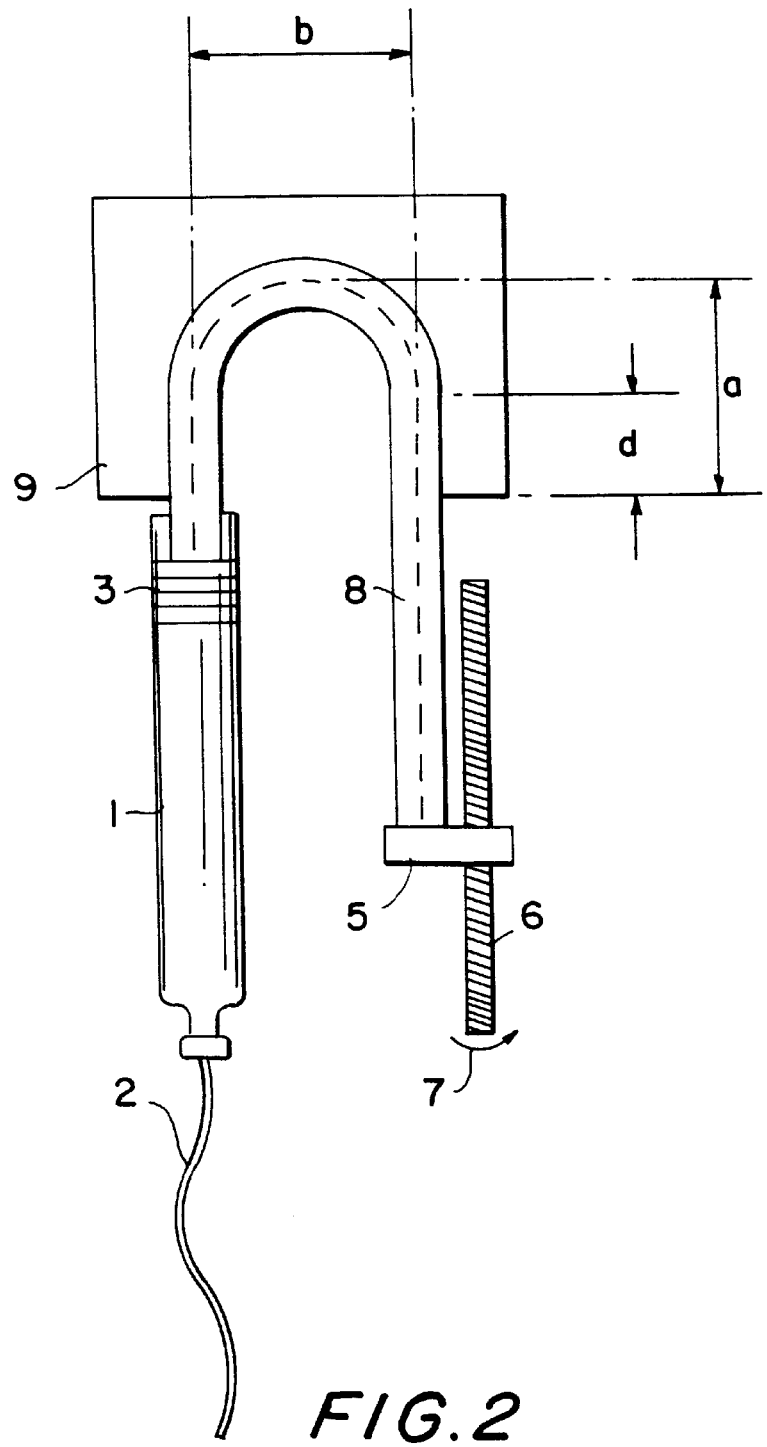

In the following the invention is described in further details with references to the drawing, wherein FIG. 1 schematically shows a known displacement system, FIG. 2 schematically shows a displacement system having a deflectable piston rod.

FIG. 1 shows schematically a displacement system of the conventional known kind. A cartridge 1 is at one end closed by a closure enabling the mounting of a catheter 2 communicating with a liquid medicine in the cartridge. At its other end the cartridge is closed by a piston 3 which by a piston rod 4 may be pressed into the cartridge to press out the liquid medicine through the catheter 2. The pressure advancing the piston 3 in the cartridge 1 is transmitted to the end of the piston rod through a presser foot 5 which is advanced by a threaded drive spindle by having a bore with an internal thread engaging the thread of the drive spindle 6, which spindle as shown by the arcuate arrow 7 is rotated by a not shown drive mechanism controlling the rate at which the medicine is pressed out through the catheter. The Cartridge 1 and the drive spindle 6 are mounted in a housing, not shown, so that the cartridge 1 and drive spindle 6 may not be displaced relative to each other. The presser foot 5 may abut the end of the piston rod 4 or it may be secured to this end.

A displacement system according to the invention is shown in FIG. 2. This system comprises to some extent the same elements as do the system shown in FIG. 1 and these elements are numbered as the corresponding elements in FIG. 1. However, a flexible piston rod 8 replaces the conventional stiff piston 4 rod of FIG. 1. Further a piston rod guide 9 is provided which guide deflects the piston rod 8 immediately outside the open end of the cartridge 1.

In the embodiment shown in FIG. 2 the piston rod 8 is deflected 180° so that the outer end of this flexible rod 8 runs parallel with the cartridge whereby the overall length of the device may be reduced to correspond to about the length of the cartridge and the deflecting piston rod guide 9.

The piston rod guide 9 is equipped with a guiding track conforming the outer contour of the bended or deflected piston rod 8 so that the deflection is guided and no bending of the rod 8 is possible except for the deflection defined by the guide 9.

The guiding track is guiding the piston rod over a length "a" which in the axial direction of the parallel ends of the rod 8 is as long as or longer than the distance "b" between the two axes of the parallel straight portions of the piston rod 8 projecting from the piston rod guide 9. Each end of the guiding track are linear along a distance "d" whereby it is ensured that no deflecting forces have to be exerted on the piston rod 8 outside the piston rod guide 9.

In the embodiment shown in FIG. 2 the driving force is exerted on the outer end of the deflected piston rod 8. The force is exerted in the axial direction of said outer end and due to the rod 8 being incompressible and the guide guiding the rod conforming with the profile of the flexible rod, the piston rod is displaced along its own axis round through the bending provided by the guide 9 to drive the piston 3 into the cartridge 1. The drive mechanism comprising a presser foot 5 acting on the free end of the piston rod 8 and a threaded spindle 6 engaging an internal thread in a bore in the presser foot 5 may be of any known type providing a rotation in the direction indicated by the arcuate arrow 7.

The flexible piston rod may be advanced by other mechanisms and the driving force may be transmitted to the flexible rod anywhere along its length without deviating from the scope of the invention.

We claim:

1. A displacement system for controlled infusion of a liquid from a cartridge, said system comprising:

a tubular vessel having a front end and a rear end, the rear end being closed by a piston which is movable by a piston rod moving into the vessel in the axial direction thereof to press out the liquid through an outlet arranged at the front end of the vessel, the piston rod being a flexible incompressible construction which at a position behind the rear end of the tubular vessel is deflected away from the axis of the cartridge by a piston rod guide provided behind the rear end of the cartridge and deflects the piston rod 180° so that parallel portions of the piston rod projects from one side of the piston rod guide, the piston rod guide has a guide track having an upper curved part and a lower linear part at each end of the curved part, each of the linear parts having a first length in the direction of the projecting parallel portions, said first length for each of the linear parts extending from a side of the piston rod guide from which the respective portion projects to an end of the curved part, a second length taken from said side of the piston rod guide to the center of the piston rod at the top of the curved part, said second length being equal to the sum of the length of one of the linear parts plus the radius of the curved part, said second length being equal to or larger than the distance between the axes of the two extending parallel portions, wherein the piston rod is formed by a flexible helix with narrowly adjacent turns of windings, the flexible helix having a coiling ratio $$r_{coil} = [d_{helix-dwire}] \div d_{wire} < 5.0,$$

where $d_{helix}$ is an outer diameter of the wound helix, and $d_{wire}$ is a diameter of the wire.

2. A displacement system according to claim 1, wherein the curved part of the guiding track has in the shape that the curved part of the piston rod will spontaneously adopt when its end portions are kept parallel.

3. A displacement system according to claim 1, wherein $r_{coil} < 4.5$.

4. A displacement system according to claim 3, wherein $r_{coil} < 4.0$.

5. A displacement system according to claim 4, wherein $r_{coil} < 3.5$.

6. A displacement system according to claim 1, wherein the windings of the helix provide an external thread.

7. A displacement system according to claim 6, further comprising a piston rod drive for transmitting a drive force to the piston rod through a nut element having an internal thread engaging the external thread of the piston rod.

8. A displacement system according to claim 1, wherein the driving force is transmitted to the piston rod at a linear part of the rod.

9. A displacement system according to claim 8, wherein the driving force is transmitted to the piston rod at a part thereof disposed between the rear end of the cartridge and the piston rod guide.

10. A displacement system according to claim 1, wherein a driving force is exerted on a free, deflected end of the piston rod in the axial direction.

11. A displacement system according to claim 1, wherein said length for each of the linear parts are substantially equal.

* * * * *

UNITED STATES PATENT AND TRADEMARK OFFICE
CERTIFICATE OF CORRECTION

PATENT NO.    : 5,957,889                                    Page 1 of 1
DATED         : September 28, 1999
INVENTOR(S)   : Poulsen et al.

It is certified that error appears in the above-identified patent and that said Letters Patent is hereby corrected as shown below:

Column 5,

Line 8, please delete "$r_{coil} = [d_{helix} - d_{wire}] \div d_{wire} \quad < 5.0,$" and insert
-- $r_{coil} = [d_{helix} - d_{wire}] \div d_{wire}] \quad < 5.0,$ --.
Line 13, please delete ""in".

Signed and Sealed this

Twenty-ninth Day of January, 2002

Attest:

JAMES E. ROGAN
Attesting Officer        Director of the United States Patent and Trademark Office